US012357216B2

(12) United States Patent
Kouider et al.

(10) Patent No.: US 12,357,216 B2
(45) Date of Patent: Jul. 15, 2025

(54) PORTABLE ELECTROENCEPHALOGRAPHY DEVICES

(71) Applicant: NextMind SAS, Paris (FR)

(72) Inventors: Sid Kouider, Paris (FR); Hao Zhang, Suresnes (FR); Antoine Goupille, Paris (FR); Jeanne Vicerial, Pantin (FR); Guillaume Ployart, Paris (FR); Arthur Biancarelli, Paris (FR); Gaelle Gervais, Paris (FR)

(73) Assignee: Snap Inc., Santa Monica, CA (US)

( * ) Notice: Subject to any disclaimer, the term of this patent is extended or adjusted under 35 U.S.C. 154(b) by 384 days.

(21) Appl. No.: 16/970,271

(22) PCT Filed: Feb. 12, 2019

(86) PCT No.: PCT/EP2019/053454
§ 371 (c)(1),
(2) Date: Aug. 14, 2020

(87) PCT Pub. No.: WO2019/158534
PCT Pub. Date: Aug. 22, 2019

(65) Prior Publication Data
US 2021/0030297 A1    Feb. 4, 2021

(30) Foreign Application Priority Data
Feb. 15, 2018  (FR) ........................... 1851287

(51) Int. Cl.
*A61B 5/00*    (2006.01)
*A61B 5/254*    (2021.01)
(Continued)

(52) U.S. Cl.
CPC .............. *A61B 5/291* (2021.01); *A61B 5/254* (2021.01); *A61B 5/31* (2021.01); *A61B 5/6803* (2013.01);
(Continued)

(58) Field of Classification Search
CPC ..................................................... A61B 5/242
See application file for complete search history.

(56) References Cited

U.S. PATENT DOCUMENTS 7,173,437 B2    2/2007  Hervieux et al.
10,076,279 B2 *  9/2018  Nahum ................... A61B 5/11
(Continued)

FOREIGN PATENT DOCUMENTS

CA    3091295 A1    8/2019
CN    103445773 A   12/2013
(Continued)

OTHER PUBLICATIONS

International Search Report issued in PCT/EP2019/053454 mailed on Apr. 11, 2019 (8 pages).
(Continued)

*Primary Examiner* — Etsub D Berhanu
(74) *Attorney, Agent, or Firm* — Schwegman Lundberg & Woessner, P.A.

(57) ABSTRACT

According to one aspect, the present description relates to a portable device (10) for acquiring electroencephalographic (EEG) signals emitted by a user. The portable device comprises a flexible support (11) intended to fit a localized region of the skull of the user and a set of sensors (13) of electrical signals generated by the neuronal activity of the user, arranged on said support (11) so as to form contacts with the scalp when the device is worn by the user. For each sensor, an electronic circuit for filtering and amplifying electrical signals detected by said sensor is incorporated in the flexible support (11) and forms, with said sensor, an active electrode. The portable device also comprises a housing (12) comprising an electronic system for processing signals from said electronic filtering and amplification circuits, said housing being linked mechanically to the flexible
(Continued)

support to form, with said support, a means of attachment to a garment or accessory intended to be worn by the user.

10 Claims, 8 Drawing Sheets

(51) Int. Cl.
    *A61B 5/291* (2021.01)
    *A61B 5/31* (2021.01)
(52) U.S. Cl.
    CPC ...... *A61B 5/6838* (2013.01); *A61B 2562/164* (2013.01)

(56) References Cited

U.S. PATENT DOCUMENTS

| | | |
|---|---|---|
| 2002/0029005 A1 | 3/2002 | Levendowski et al. |
| 2005/0215916 A1 | 9/2005 | Fadem et al. |
| 2009/0156925 A1* | 6/2009 | Jin ................. A61B 5/291 |
| | | 600/372 |
| 2013/0066183 A1 | 3/2013 | Jin et al. |
| 2013/0310676 A1 | 11/2013 | Jung |
| 2014/0316230 A1* | 10/2014 | Denison ............. A61B 5/168 |
| | | 600/545 |
| 2015/0112153 A1 | 4/2015 | Nahum |
| 2015/0112453 A1 | 4/2015 | Kern |
| 2015/0141788 A1 | 5/2015 | Chi et al. |
| 2016/0022981 A1 | 1/2016 | Wingeier et al. |
| 2016/0089045 A1* | 3/2016 | Sadeghian-Motahar ............ |
| | | A61B 5/0531 |
| | | 600/386 |
| 2016/0157777 A1* | 6/2016 | Attal ................ A61B 5/291 |
| | | 600/383 |
| 2017/0027466 A1 | 2/2017 | Kerth et al. |
| 2017/0065816 A1 | 3/2017 | Wingeier et al. |
| 2017/0258400 A1 | 9/2017 | Jovanovic et al. |

FOREIGN PATENT DOCUMENTS

| | | |
|---|---|---|
| CN | 106310517 A | 1/2017 |
| CN | 107049307 A | 8/2017 |
| CN | 112384143 A | 2/2021 |
| EP | 3752057 A1 | 12/2020 |
| EP | 3752057 B1 | 6/2024 |
| FR | 3077723 A1 | 8/2019 |
| FR | 3077723 B1 | 3/2020 |
| JP | 3626176 B1 | 12/2004 |
| JP | 2005065937 A | 3/2005 |
| JP | 2005152415 | 6/2005 |
| JP | 2009530064 | 8/2009 |
| JP | 2010538701 A | 12/2010 |
| JP | 2013508120 A | 3/2013 |
| JP | 2014036862 | 2/2014 |
| JP | 2015083212 | 4/2015 |
| JP | 2021517848 A | 7/2021 |
| JP | 2023082199 A | 6/2023 |
| JP | 7572495 B2 | 10/2024 |
| KR | 20210084343 A | 7/2021 |
| WO | WO-2013073673 A1 | 5/2013 |
| WO | 2016070188 | 5/2016 |
| WO | WO-2016140325 A1 | 9/2016 |
| WO | WO-2016166740 A1 | 10/2016 |
| WO | WO-2019158534 A1 | 8/2019 |

OTHER PUBLICATIONS

Written Opinion of the International Searching Authority issued in PCT/EP2019/053454 mailed on Apr. 11, 2019 (8 pages).
"European Application Serial No. 19708238.1, Response to Communication pursuant to Rules 161(1) and 162 EPC filed Mar. 25, 2021", 13 pgs.
"International Application Serial No. PCT/EP2019/053454, International Preliminary Report on Patentability mailed Aug. 27, 2020", w/ English Translation, 8 pgs.
"International Application Serial No. PCT/EP2019/053454, International Search Report mailed Apr. 11, 2019", w/ English Translation, 6 pgs.
"International Application Serial No. PCT/EP2019/053454, Written Opinion mailed Apr. 11, 2019", w/ English Translation, 12 pgs.
"Japanese Application Serial No. 2020-566877, Notification of Reasons for Refusal mailed Nov. 22, 2022", w/ English translation, 8 pgs.
"Korean Application Serial No. 10-2020-7026191, Office Action mailed Aug. 22, 2022", w/ English translation, 4 pgs.
"Japanese Application Serial No. 2020-566877, Response Filed Feb. 13, 2023 to Notification of Reasons for Refusal mailed Nov. 22, 2022", w/ English Claims, 8 pgs.
"Chinese Application Serial No. 201980026161.9, Office Action mailed Sep. 21, 2023", w/ English Translation, 15 pgs.
"Korean Application Serial No. 10-2020-7026191, Response filed Dec. 19, 2023 to Office Action mailed Aug. 22, 2022". w/ English Translation, 4 pgs.
"Japanese Application Serial No. 2023-061873, Notification of Reasons for Refusal mailed Apr. 2, 2024", w/ English translation, 10 pgs.
"Chinese Application Serial No. 201980026161.9, Office Action mailed Apr. 8, 2024", w/ English Translation, 16 pgs.
"Canadian Application Serial No. 3,091,295, Office Action mailed May 3, 2024", 5 pgs.
"Canadian Application Serial No. 3,091,295, Response filed Jul. 9, 24 to Office Action mailed May 3, 24", 8 pgs.
"Korean Application Serial No. 10-2020-7026191, Notice of Preliminary Rejection mailed Jul. 15, 24", W/English Translation, 30 pgs.
"Korean Application Serial No. 10-2020-7026191, Response filed Sep. 10, 24 to Notice of Preliminary Rejection mailed Jul. 15, 24", w/ English claims, 43 pgs.
"Chinese Application Serial No. 201980026161.9, Decision of Rejection mailed Nov. 8, 24", w/ English Machine Translation, 14 pgs.
"Chinese Application Serial No. 201980026161.9, Office Action mailed Jul. 29, 24", w/ English Machine Translation, 13 pgs.
"European Application Serial No. 24173679.2, Extended European Search Report mailed Aug. 16, 24", w/ English Machine Translation, 21 pgs.
"Canadian Application Serial No. 3,091,295, Office Action mailed Mar. 4, 25", 4 pgs.
"Chinese Application Serial No. 201980026161.9, Request for Reexamination filed Feb. 7, 2025", w/ English machine translation, 17 pgs.
"European Application Serial No. 24173679.2, Response filed Mar. 3, 25 to Extended European Search Report mailed Aug. 16, 24", 15 pgs.
"Japanese Application Serial No. 2024-177791, Notification of Reasons for Refusal mailed Apr. 15, 25", w/ English Translation, 20 pgs.

* cited by examiner

PORTABLE ELECTROENCEPHALOGRAPHY DEVICES

TECHNICAL FIELD OF THE INVENTION

The present invention relates to portable devices for acquiring electroencephalographic (EEG) signals or portable surface electroencephalographs, and to methods for acquiring electroencephalographic signals using these electroencephalographs.

STATE OF THE ART

Surface electroencephalography makes it possible to measure the diffuse electrical potential variations on the surface of the skull. These electrical potential variations are commonly called electroencephalographic signals or EEG signals.

A first difficulty relates to the reliability of the devices used to capture the EEG signals. Indeed, given the very low amplitude of the electrical potential variations to be measured (of the order of a few microvolts), it is necessary to ensure a maximum conductivity between the electrode and the scalp in order to obtain a usable EEG signal, and therefore a perfect contact, which can prove difficult notably because of the hair of the user.

Several solutions are now used in the current devices to address the signal reliability constraint.

Some surface electroencephalographs are equipped with gel electrodes, in which the contact is made through a gel or a conductive liquid, which is easily infiltrated through the hair of the user to reach the scalp. The gel makes it possible to reduce the electrical impedance and thus the interferences with surrounding signals. This solution makes it possible to obtain a good conductivity at any point of the scalp. However, this type of device requires technical assistance for the placement of the electrodes. In particular, this solution is time-consuming (the gel is placed and the conductance verified on each electrode one by one). Furthermore, it limits the time of use of the device to a few hours (when the gel dries, the contact is no longer assured).

More recently, surface electroencephalographs with dry, so-called "active" electrodes have been developed. Such electrodes are for example described in the published patent application US 20133066183. The function of the active dry electrodes is to pick up the electrical potential variations on the surface of the scalp, and to filter them and amplify them. The analog signals thus obtained are then converted into digital signals by means of one or more analog-digital converters controlled by a microcontroller. The microcontroller receives the data to analyze them, to store them or to transmit them to another device.

In the active dry electrodes, the contact with the scalp is made through solid conductive elements or "sensors" linked to an electronic circuit that makes it possible to overcome the increased impedance due to the absence of gel. The active electronic component makes it possible to ensure a signal capture comparable to that of a gel electrode. An additional advantage of the active electrode is that it makes it possible to filter and/or amplify the signals, and thus improve the signal-to-noise ratio. However, the main difficulty with this technique is access to the scalp.

The current solutions generally use sensors based on polymer and with pins by exerting a significant pressure to reach the scalp of the user (see for example the published patent application US 2015141788). While this approach can allow a good contact with the scalp, it has the major drawback of being very uncomfortable, above all for prolonged use.

Moreover, another difficulty in the design of the surface electroencephalographs concerns the acceptability of the EEG with the public, which dictates esthetic constraints and constraints related to comfort and ease of use.

Indeed, the systems intended for the medical field or for research generally comprise a bonnet, made of elastic or impermeable fabric, with locations intended to accommodate the sensors, the electronic circuits linked to the sensors and the housing of the acquisition system. They are thus formed by three distinct elements that the operator/attendant must assemble on each use.

Portable devices for acquiring EEG signals have been proposed which allow a user to dispense with the assistance of a specialist technician. The patent application US 2002/0029005 for example describes headgear for the acquisition of EEG signals with predetermined locations for the electrodes and adjustable elastic bands making it possible to ensure the contact of the electrodes against the scalp. Such a device is however still complex in its use because of the large number of distinct and adjustable parts.

The patent application US 2017/0027466 also describes a portable device for acquiring EEG signals that can be used without assistance, and in which the number of removable and adjustable mechanical parts is reduced, allowing a simpler and rapid use for an inexperienced user. For this, the EEG signal acquisition device comprises a central part intended to be positioned on the top of the head and that can house all of the electronic components. From the central part, long and short arms extend all around the head, at the end of which sensors are positioned. At least some of these arms are elastic or have spring functions which allow the head to be gripped while adapting to its contour, with a sufficient force to ensure the necessary contact of the sensors with the scalp. In addition to the lack of discreetness of such a device, the latter has the drawback of being very uncomfortable since, unless a straight vertical head position is maintained, the gripping force passes exclusively through the sensors, which generates very localized points of strong pressure.

The patent application US 2016/157777 also describes a portable device for the acquisition of EEG signals comprising a central part intended to be positioned on the top of the head, and from which long and short arms extend, at the end of which sensors are positioned. All of the electronic components can be housed within the central part or one of the flexible branches.

The patent applications US 2015/112453 and US 2017/258400 describe portable devices for acquiring EEG signals in which at least some of the electronic components can be housed in assemblies that can be connected to an electronic connector of the device. In the device described in patent application US 2015/112453, the assembly can be connected detachably.

The devices described, even though they make it possible to dispense with the technical support of an operator and offer solutions that make it possible to ensure a satisfactory contact with the scalp of the user, lack the necessary discreetness, notably for consumer applications, such as, for example, video games, training, sleep assistance, etc.

The present description proposes portable surface electroencephalographs equipped with active dry electrodes which offer, as well as an excellent signal quality, great ease of use, comfort for the user and great discreetness. Such surface portable electroencephalographs will be able to be used in a hospital environment, for example for ambulatory patients in a clinical diagnostic context, but also make it possible to promote the emergence of new fields of application for electroencephalography.

SUMMARY

According to a first aspect, the present description relates to a portable device for acquiring electroencephalographic (EEG) signals emitted by a user, the device comprising:
- a flexible support intended to fit a localized region of the skull of the user;
- a set of sensors for detecting electrical signals generated by the neuronal activity of the user, arranged on said support so as to form contacts with the scalp when the device is worn by the user;
- for each sensor, an electronic circuit for filtering and amplifying the electrical signals detected by said sensor, said electronic circuit being incorporated in the flexible support and forming, with said sensor, an active electrode;
- a housing comprising an electronic system for processing the signals from said electronic filtering and amplification circuits, said housing being linked mechanically to the flexible support to form, with said support, a means of attachment to a garment or accessory intended to be worn by the user.

In the device thus described, the electronic components handling the various electronic functions are distributed between the flexible support and the housing, the latter cooperating mechanically to form a means of attachment to a garment or accessory. That makes it possible to both make the support intended to be in contact with the skull of the user more flexible and thinner, typically with a thickness less than 10 mm, or even a thickness less than 5 mm, and to make the device extremely easy to use, with no loss of quality of the EEG signals acquired. The portable device thus described therefore offers performance levels that are at least comparable to those of the devices of the state of the art, but also an ease of use and ergonomics compatible with consumer applications. The portable device is applied to man but can also be applied to certain animals, the device being non-invasive and having qualities of precision and comfort that lend themselves to use in research on animals.

The number of sensors arranged on the flexible support depends on the application. This number can, for example, be between 2 and 128, or even more. According to the application envisaged, the support can either cover a limited zone of the skull to measure the cerebral activity generated by a precise zone of the brain, for example the visual, auditory, motor, somatosensorial, or prefrontal cortex, or extend over all of the surface of the skull. It will be possible to determine the number of sensors based on the surface covered by the support and the desired spatial resolution.

According to one or more embodiments, the flexible support and the housing are linked mechanically by an attachment point, for example an off-center attachment point, to form, between the housing and the support, a gap making it possible to allow a garment and/or an accessory to pass through. Advantageously, said gap is between 2 mm and 5 mm.

According to one or more embodiments, the attachment point is flexible, making it possible to form a "clip" or clamp form attachment means.

According to one or more exemplary embodiments, the attachment point also allows the electrical contact between the electronic components housed in the flexible support and those housed in the housing.

According to one or more embodiments, the attachment point is detachable.

According to one or more embodiments, the electronic signal processing system housed in the rigid housing comprises one or more analog/digital converters (ADC) intended to transform the signals from the electronic filtering and amplification circuits into digital signals and a microcontroller, notably for the transmission to an external processing unit and/or the storage of said digital signals. The rigid housing can of course house other electronic elements, for example a battery, and/or other types of sensors, for example an accelerometer and/or a gyroscope.

According to one or more embodiments, the flexible support is openwork; for example, the flexible support comprises a plurality of branches on which at least some of said sensors are arranged. This structure gives the support a greater flexibility and allows a better adaptation to the shape of the skull.

For example, the sensors are distributed on 2 to 6 branches.

According to one or more embodiments, the branches are parallel, which makes it possible to apply a more uniform pressure on the sensors even when the garment or utensil does not cover all of the support, and makes it easier to understand the translational gesture that a user will be able to make to put the device in place.

According to one or more embodiments, 2 branches or more can be linked to a central part by means of flexible lateral branches.

According to one or more embodiments, 3 branches or more can be arranged parallel in comb form.

According to one or more embodiments, each sensor is movably mounted on said flexible support, for example by means of a mechanical link of spring type, which makes it possible to improve the contact with the scalp.

According to one or more embodiments, the mechanical link of spring type comprises a spring finger forming a contact point with a base of said sensor, allowing a mobility of the sensor according to several axes.

According to one or more embodiments, said spring finger ensures the electrical contact of said sensor with said filtering and amplification circuit.

According to one or more embodiments, each sensor comprises a base intended to be arranged in a recess of the flexible support, in electrical contact with said filtering and amplification circuit.

According to one or more embodiments, each sensor comprises a plurality of conductive blades, arranged on said base, with said conductive blades being intended to form linear contacts with the scalp when the device is worn by the user.

Such a linear contact makes it possible to have a greater contact surface area and, thereby, a better sensitivity and comfort for the user.

According to one or more embodiments, the conductive blades are arranged substantially parallel. When at least some of the sensors are arranged on parallel branches of the support, the conductive blades are advantageously parallel to said branches.

According to one or more exemplary embodiments, each sensor comprises two conductive blades. The number of two conductive blades is a good compromise because it makes it possible to distribute the contact pressure while keeping a good measurement accuracy.

According to one or more embodiments, the edge-to-edge spacing between said two conductive blades is greater than 2 mm, to allow the hair to pass through. Advantageously, said spacing is less than 50 mm, advantageously less than 10 mm so as not to lose accuracy. For example, said spacing is between 2 mm and 6 mm.

According to one or more embodiments, the conductive blades comprise a conductive polymer coating forming a conductive layer intended to enter into contact with the scalp of the user.

According to one or more embodiments, the conductive blades have at least one point (conductive or not) intended to enter into contact first with the scalp when the support is positioned on the skull. The effect of this point is to separate the hair when placing the device, so as to expose the scalp of the user to the conductive blades.

According to a second aspect, the present description relates to a connected garment or accessory for the acquisition of electroencephalographic (EEG) signals comprising a portable device according to the first aspect.

This garment or accessory can for example be a headband, headgear, a headset, etc.

According to a third aspect, the present description relates to a method for acquiring electroencephalographic (EEG) signals emitted by a user by means of a portable device according to the first aspect, comprising:
- the measurement of electrical signals generated by the neuronal activity of the user by means of said sensors in contact with the scalp of the user;
- the processing of the electrical signals from said filtering and amplification circuits by means of the electronic processing system arranged in said housing.

According to one or more embodiments, said processing of the electrical signals comprises the analog/digital conversion of the electrical signals from said filtering and amplification circuits and the transmission of said digital signals to an external processing unit and/or the storage of said digital signals.

BRIEF DESCRIPTION OF THE FIGURES

Other advantages and features of the invention will become apparent on reading the description, illustrated by the following figures, which represent.

DETAILED DESCRIPTION

Figure 1A:
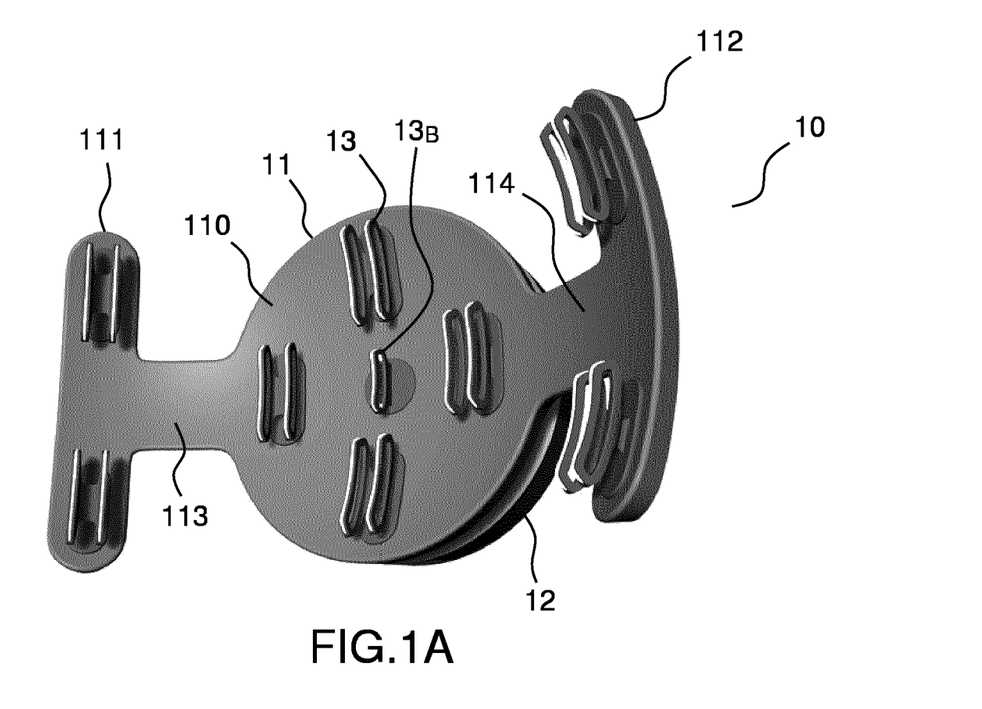
FIGS. 1A-1E, different views of a first example of a portable device for acquiring EEG signals according to the present description.
Figure 1B:
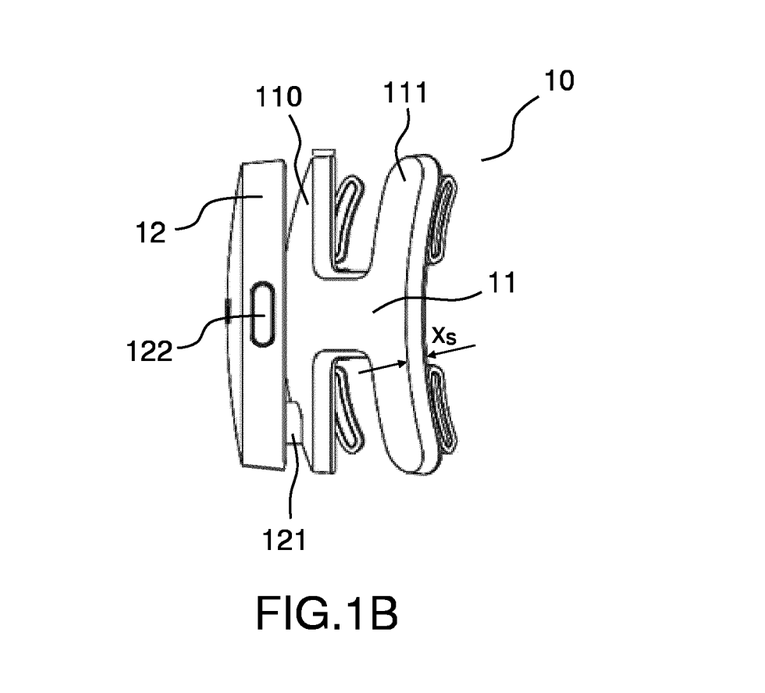
Figure 1C:
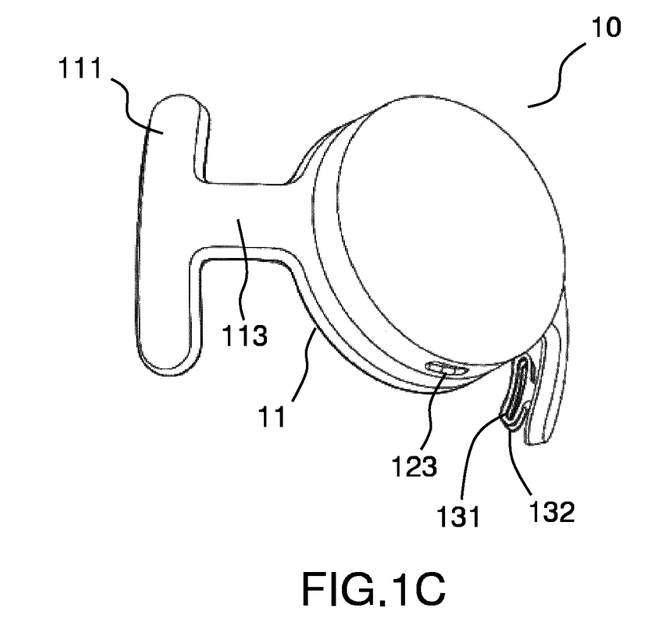
Figure 1D:
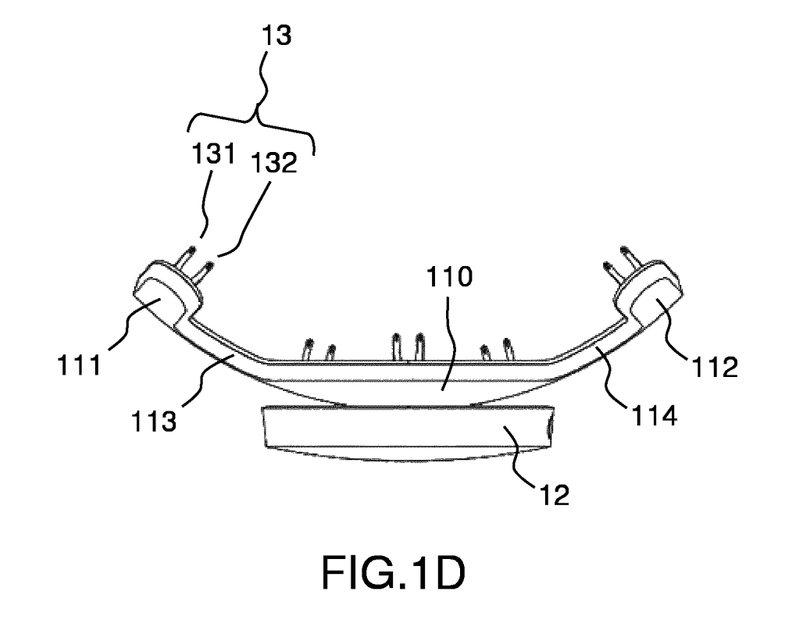
Figure 1E:
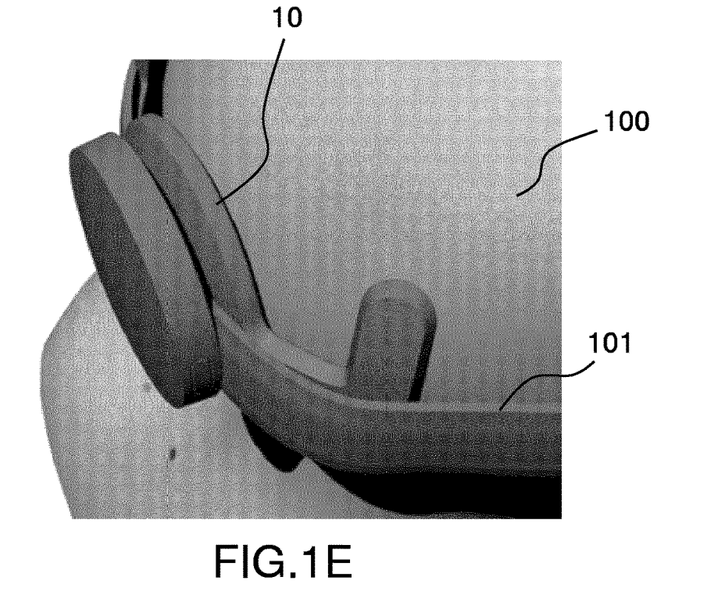

FIGS. 1A-1D respectively represent a front view, a first side view, a back view and a second side view of a first example of a portable device 10 for acquiring EEG signals according to the present description, while FIG. 1E illustrates a view of the device worn by a user.

The portable device as illustrated in FIGS. 1A to 1D comprises a flexible support 11 intended to fit a localized region of the skull of a user, for example the occipital region at the rear of the skull, and a housing 12 linked mechanically and electronically to the flexible support 11. On the support, there are arranged a set of sensors 13 for detecting electrical signals generated by the neuronal activity of the user. An additional, so-called grounding or "bias", electrode 13B is provided to eliminate the common mode from the signals measured by the other sensors. As will be described in more detail hereinbelow, each sensor can comprise a plurality of conductive blades (in this example, two conductive blades 131, 132), for example arranged substantially parallel, so as to form linear contacts with the scalp when the device is worn by the user; these conductive blades can also be deformable by pressure on the scalp of the user. Each sensor forms, with an electronic circuit for filtering and amplifying electrical signals (not represented in FIGS. 1A-1D), an active electrode. The signals from the electronic filtering and amplification circuits are processed by an electronic system comprising, for example, as will be described hereinbelow, one or more analog/digital converters (ADC) and a microcontroller that notably makes it possible to store and/or transmit processed signals outside the device. The electronic system is incorporated in the housing 12 while the electronic filtering and amplification circuits of the active electrodes are incorporated in the flexible support. The separation of the electronic components respectively in the support on which the sensors are arranged and in the housing allows for a great design versatility of the support 11, notably in terms of form, of thinness and of mechanical flexibility. Thus, for example, the thickness $X_S$ of the flexible support can advantageously be less than 10 mm, for example between 2 mm and 10 mm, and can advantageously be less than 5 mm, for example between 2 mm and 5 mm. The housing can of course house other electronic elements necessary to the operation of the device, for example a battery and/or other types of sensors, for example an accelerometer and/or a gyroscope. In the example of FIGS. 1A-1D, the housing 12 is also equipped with an ON/OFF switch 122 and a connection port 123, for example a USB port.

Moreover, as is illustrated in FIGS. 1A-1E, the support 11 and the housing 12 cooperate to form a means of attachment to a garment or accessory intended to be worn by the user. Thus, in this example, the housing 12 is linked to the support 11 by an off-center attachment point 121 to form, between the housing and the support, a gap allowing a garment and/or an accessory to pass through, typically a gap of a few millimeters, for example between 2 mm and 5 mm. In this example, the attachment point is flexible so as to form a clamp or "clip", in which the garment or an accessory, for example a headband 101 as illustrated in FIG. 1E, can be passed. The elastic headband can then make it possible to press the flexible support against a skull 100 of the user. The attachment point 121 also forms an electrical link between the filtering and amplification circuits of the active electrodes and the electronic system of the housing. For example, the attachment point comprises a sleeve in which electrical connections can pass. The attachment point can also be detachable.

Advantageously, the form of the support is designed so as to guarantee an equitable distribution of the pressure between the different sensors when the device is worn by the user. In the example of FIGS. 1A-1D, the flexible support 11 is openwork, and comprises outer branches 111, 112 linked to a central part 110 by means of lateral branches 113, 114 which give the assembly a flexibility. The sensors are arranged on the outer branches and the central part. In this example, the central part 110 is substantially round and is superposed on the housing, with the round form of the housing facilitating grip with the hand.

In the example of FIGS. 1A to 1E, two outer branches are represented, arranged laterally to, with the central part, allow a distribution of the sensors over the zone of interest of the skull. Depending on the needs, other branches supporting sensors could be provided; for example a third branch and a fourth branch for positioning sensors on the lateral parts of the skull.

Obviously, other forms are possible for the flexible support 11, notably openwork forms.

Figure 2A:
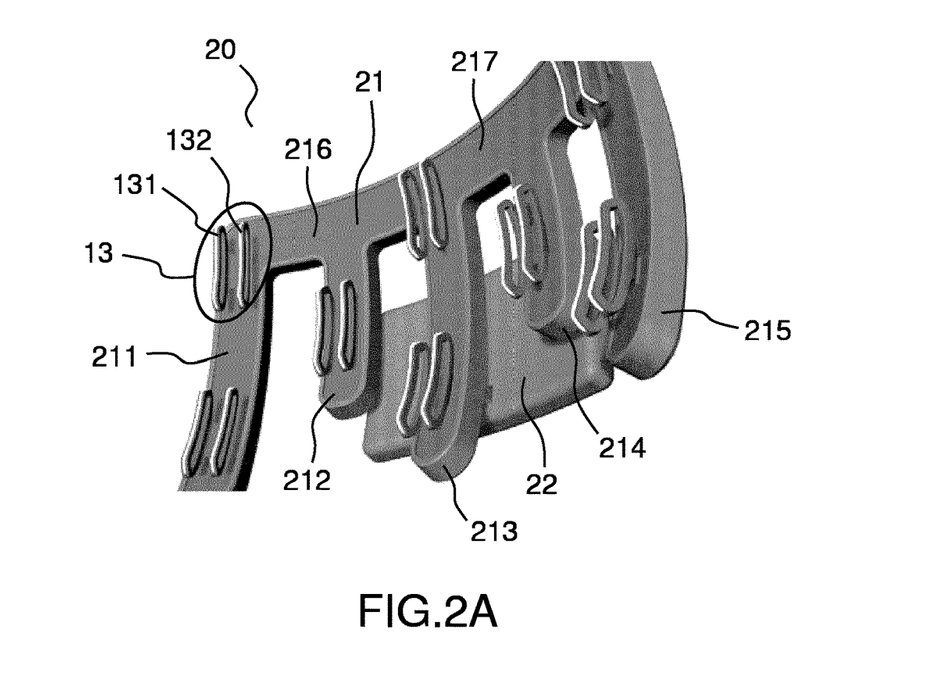
FIGS. 2A-2C, different views of a second example of a portable device for acquiring EEG signals according to the present description.
Figure 2B:
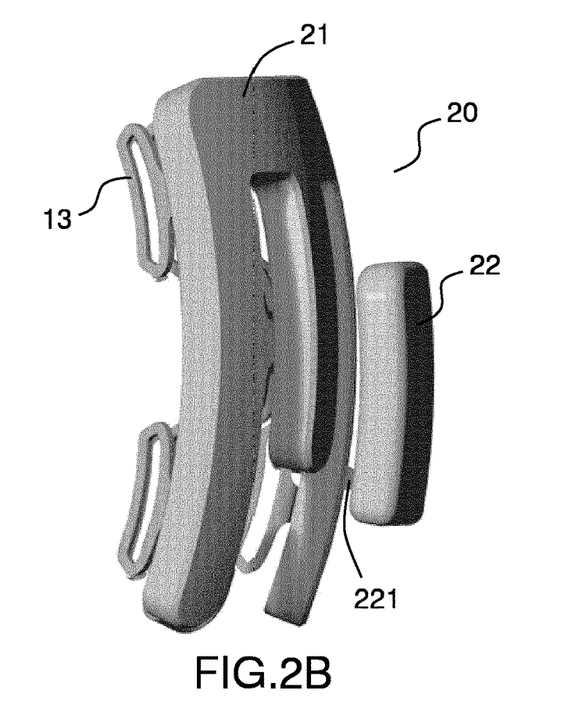
Figure 2C:
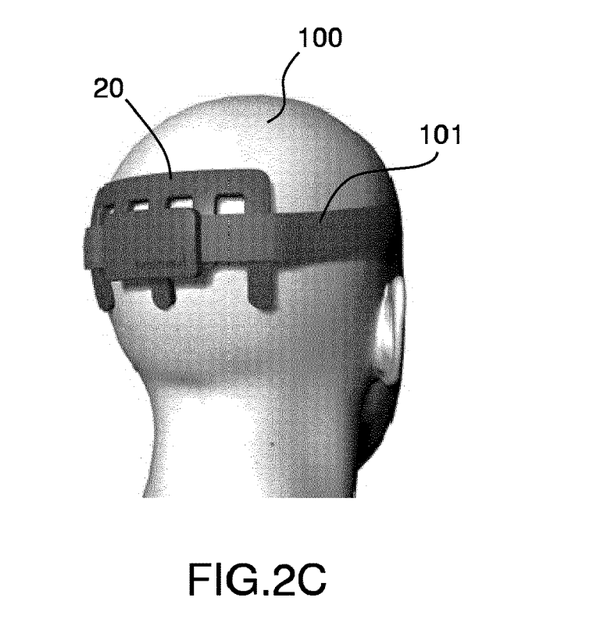

Thus, FIGS. 2A-2C illustrate a second example of a portable device 20 for acquiring the EEG signals according to the present description.

FIGS. 2A and 2B respectively illustrate a front view and a side view, while FIG. 2C shows the device 20 borne by a user by means of a headband 101. The portable device comprises a flexible support 21 intended to fit a localized region of the skull of a user and a rigid housing 22 linked mechanically and electronically to the flexible support 11. The flexible support 21 is intended to support, as in the preceding example, sensors 13, each sensor forming, with a filtering and amplification circuit (not represented), and active electrode.

In this example, the support 21 is also openwork to allow a better flexibility. In this example, it comprises a given number of branches 211-215 all arranged parallel and on which the sensors 13 are arranged. Although a grounding electrode is not represented in these figures, it can of course be provided, as in the preceding example. In this example once again, the branches 211-215 which bear the sensors are linked by lateral branches 216-217 which give the assembly flexibility.

In this example, the housing 22 and the support 21 to which it is linked by an attachment point 221, cooperate to form, as in the preceding example, a means of attachment to a garment or accessory. Thus, as illustrated in FIG. 3C, a headband 101 can be inserted in the gap formed between the support 21 and the housing 22 to hold the device 20 against the skull 100 of the user.

Figure 3A:
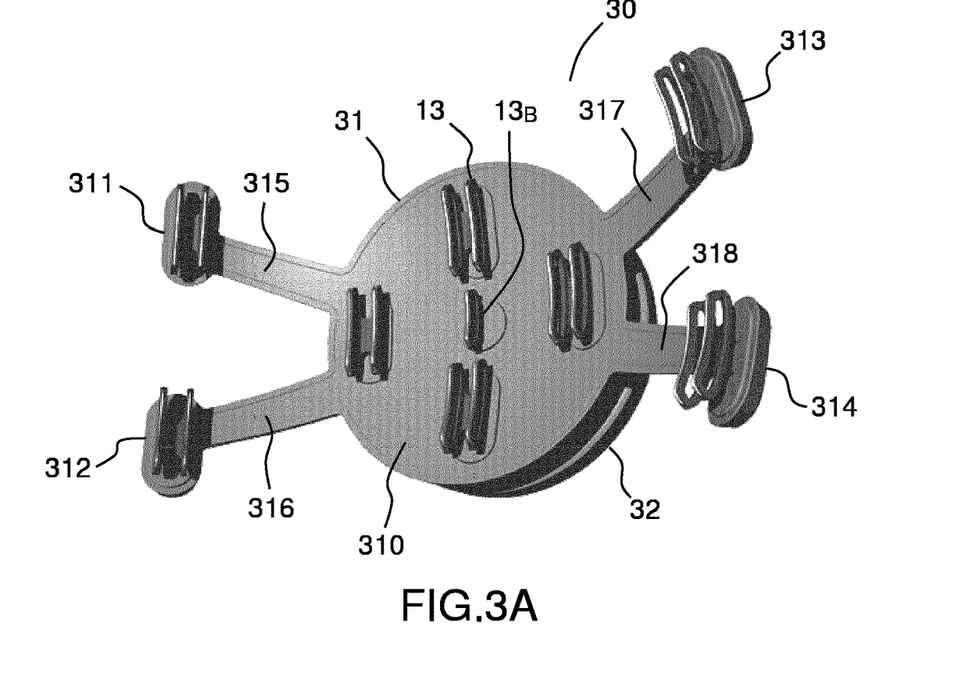
FIGS. 3A and 3B, different views of a third example of a portable device for acquiring EEG signals according to the present description.
Figure 3B:
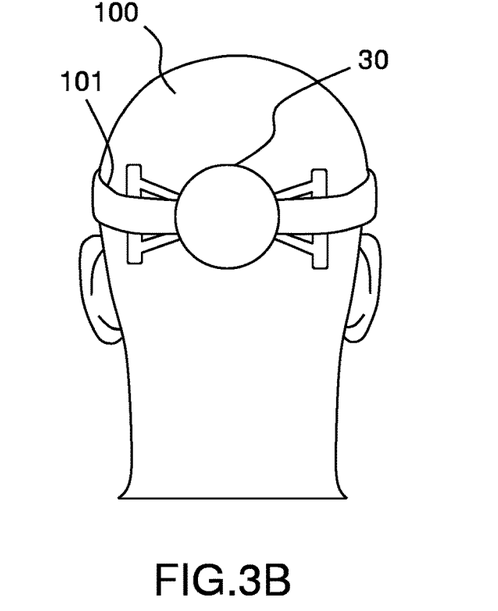

FIGS. 3A-3B illustrate a third example of a portable device 30 for acquiring EEG signals according to the present description.

In this example once again, the portable device 30 comprises a flexible support 31 and a housing 32 linked mechanically to form a means of attachment to a garment or utensil. Moreover, the support 31 and the housing 32 are connected electrically. The support 31 is, in this example, openwork so as to form a central part 310 and a set of outer branches 311-314 linked to the central part by lateral branches 315-318 which make it possible to give the support flexibility. In this example as in that of FIGS. 1A-1E, the central part 310 of the support is substantially round and its form is superposed on that of the housing 32 to allow a better grip by a user. A set of sensors 13 are arranged on the central part and on the outer branches of the support 31, as well as a grounding electrode 13B.

In the examples illustrated in the preceding figures, notably FIGS. 1E, 2C, 3B, the portable device (respectively 10, 20 and 30) is pressed against the skull of the user by means of a headband 101. It will easily be understood that the attachment means formed by the housing and the support can be applied to any other type of garment or accessory, for example a headset or any type of headgear, for example with an elastic band intended to pass between the support and the housing, an audio headset (for wearing on the top of the skull), a virtual or augmented reality headset, a hard hat, a cycle helmet, a surgeon's cap, a protective mask, etc. The attachment means formed by the support and the housing can be adapted to the type of garment or accessory to which it is intended to be attached. Any type of device, scratch tab, snap fastener, mechanical or magnetic clip, can be provided to facilitate the securing of the garment or accessory in the attachment means formed by the flexible support and the housing.

In practice, it will be possible to "clip" the portable device onto the garment or accessory, before it is worn by the user, or, on the other hand, it will be possible to "clip" the portable device onto the garment or the accessory once the latter is positioned on the head of the user.

As illustrated in the preceding figures, the conductive blades can advantageously be all substantially parallel, which makes it possible to position the support on the skull by a translational gesture parallel to the direction of the conductive blades, for example from the top of the head to the bottom of the head when it is a device intended to be worn in an occipital region of the skull. For reasons of comfort and of quality of the contact, in fact, the translational movement preferably follows the direction and line of the lay of the hair.

The various branches of the supports which support the sensors can also be substantially parallel, and parallel to the line of the conductive blades, as appears for example in FIGS. 1A-1E and 2A-2C. This offers esthetic, mechanical and ergonomic effects. In fact, the parallel branches make it possible to correctly apply the pressure at the sensors with a headband not entirely covering the support. Thus, the headband bears on the parallel branches and presses the electrodes at the ends. The branches that are thus arranged parallel to the conductive blades make it possible to minimize the visible part of the support when it is worn and make it easier to understand the translational gesture necessary to the placement of the device.

Figure 4:
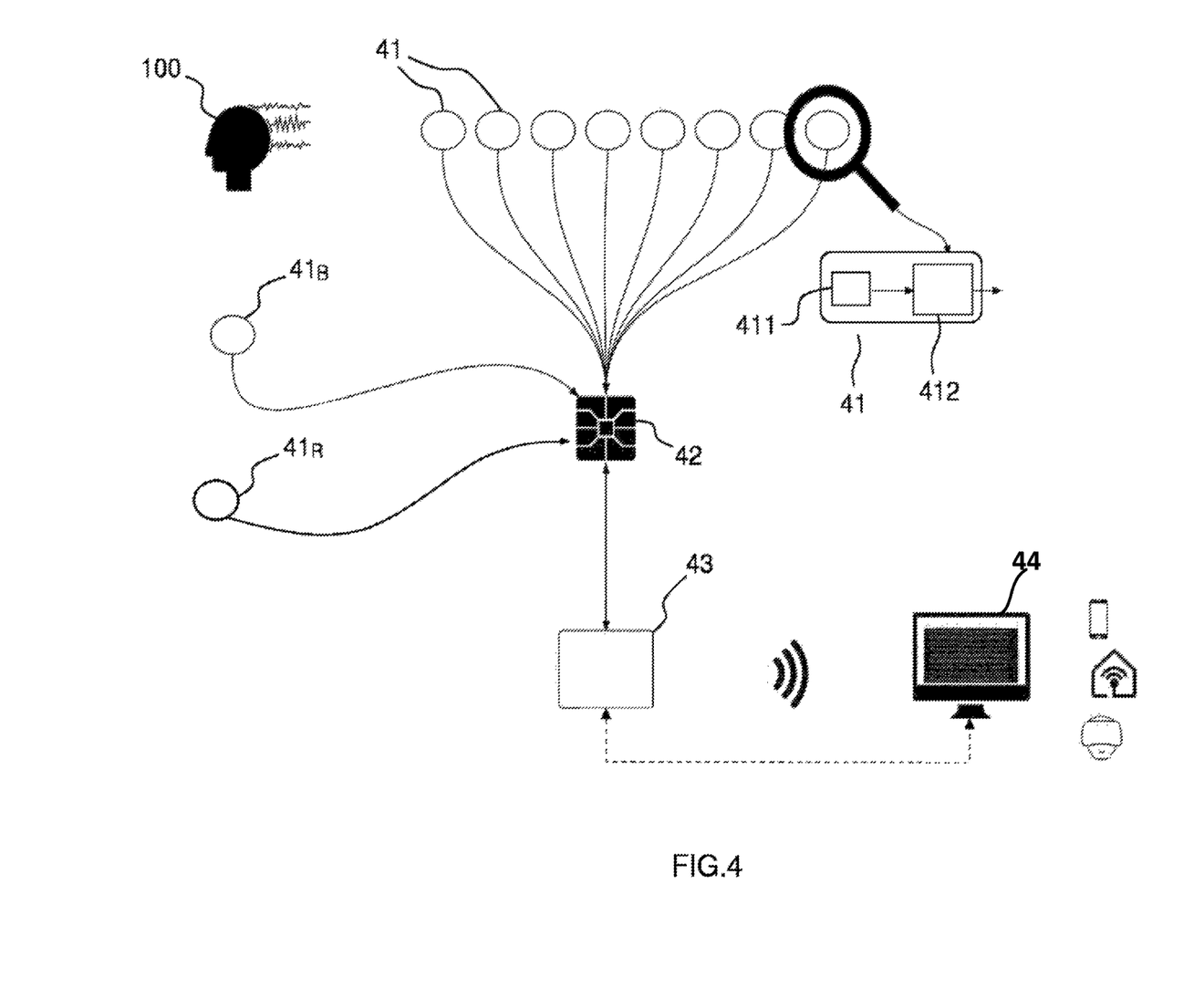
FIG. 4, an example of electronic architecture for the reception and processing of the EEG signals by means of a portable device according to the present description.

FIG. 4 illustrates an example of an electronic architecture for the reception and the processing of the EEG signals by means of a portable device according to the present description.

As described previously, the portable device according to the present description comprises a given number of active electrodes 41, for example between 2 and 128, advantageously between 2 and 64, or advantageously between 4 and 16. Each active electrode 41 comprises a sensor 411 for detecting electrical signals generated by the neuronal activity of the user 100 and an electronic filtering and amplification circuit 412. For example, each electronic circuit 412 comprises a first-order high-pass analog filter, an amplifier and a first-order low-pass analog filter. The filters make it possible to eliminate, from the signals picked up, the frequency-domain components that are useless for the envisaged application. The amplification makes it possible to adapt the amplitude of the signals to the specifications of the ADC and obtain a maximal resolution in the conversion. As illustrated in FIG. 4, the portable device also comprises one or more reference electrodes 41B and a so-called "bias" or grounding electrode 41R. The active electrodes are connected to one or more analog-digital converters 42 (ADC), with each ADC being able to convert the signals from a given number of active electrodes, for example between 1 and 128. The one or more reference electrodes 41B are connected to all the converters. The reference electrode or electrodes are preferably positioned in contact with the head of the user in a region remote from that of the other active electrodes; for example, they can be connected using a connection port such as the port 123 represented in FIG. 1C and placed in contact with the ear, or held by the garment or accessory to which the portable device is attached. The converters 42 are controlled by a microcontroller 43 and communicate therewith, for example, by the SPI (Serial Peripheral Interface) protocol. The microprocessor encapsulates the data received then transmits them to an external processing unit 44, for example a computer, a cell phone, a virtual reality headset, a motor vehicle or an aeronautical computer system, for example of car or airplane onboard computer type, for example by Bluetooth, Wi-Fi (Wireless Fidelity) or Li-Fi (Light Fidelity) technology. All the components of the acquisition system are powered by a battery (not represented in FIG. 4) housed in the housing.

According to a mode of operation of the portable device according to the present description, each active electrode measures an electrical potential value from which the potential measured by the reference electrode is subtracted ($E_i = V_i - V_{ref}$), and it is the result of this difference which is digitized by means of the ADC 42 then transmitted by the microcontroller 43. To do this, as illustrated in FIG. 4, the device comprises a given number of active measurement electrodes, for example between 2 and 64, advantageously between 4 and 16, one or two active reference electrodes 41B and the additional grounding contact 41B ("bias" electrode).

Figure 5A:
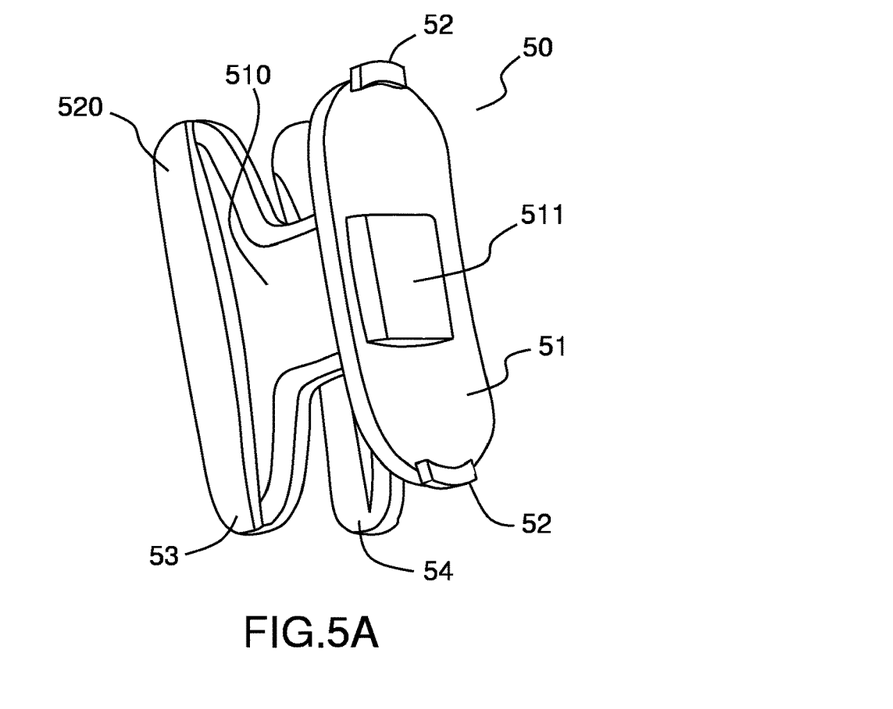
FIGS. 5A, 5B, embodiments of a sensor according to the present description, and FIG. 5C, another example of a sensor according to the present description.
Figure 5B:
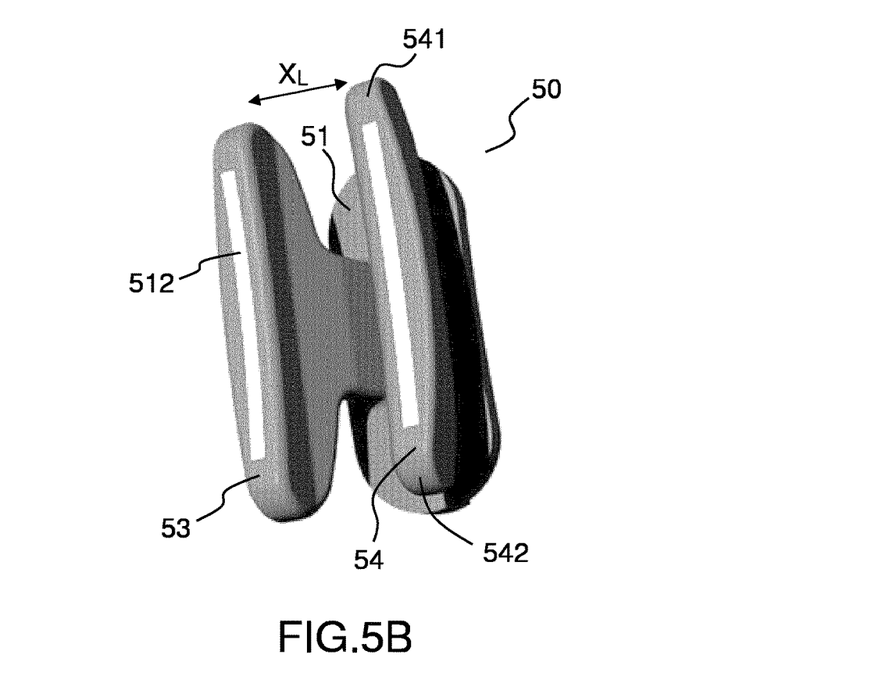

FIGS. 5A and 5B illustrate two views of an example of a sensor according to the present description.

In this example, the sensor 50 comprises a base 51 intended to be housed in a location of the flexible support (not represented) by means of a fixing device 52, and several conductive blades 53, 54. The conductive blades form a linear contact with the scalp when the device is worn by the user. A linear contact offers the advantage of forming a fairly large contact surface area with the scalp, allowing a better sensitivity in the reception of the signals and a better comfort for the user. Moreover, when the conductive blades are arranged substantially parallel, the linear contacts thus formed are compatible with a translational movement which separates the hair when the device is put in place.

The applicants have shown that a number of 2 conductive blades was optimal. With just one blade per sensor, there can be an instability in the contact formed by the blade on the scalp and the distribution of the pressure on a sole blade can present a discomfort for the user. The applicants have shown that 2 blades were suitable for covering a sufficiently small surface area of the skull and thus have a good signal accuracy. The spacing between the blades addresses a compromise between the requirement to be able to allow the hair to pass through, the measurement of the signal and the distribution of the pressure for the comfort of the user. Advantageously, the two blades are spaced apart sufficiently to be able to allow the hair to pass through. For example, the edge-to-edge distance XL between the two blades is greater than 2 mm. The maximum distance between the blades depends on the total surface area that is to be covered and on the number of sensors. However, so as not to lose accuracy, it is preferable to have a distance less than 50 mm, advantageously less than 10 mm. For example, the distance XL is between 2 and 6 mm.

In the example of FIGS. 5A and 5B, the sensor 50 comprises a metal structure 510 incorporated in a plastic part 520. The metal structure forms, at the base 51, a contact 511 which will make it possible to ensure the passage of the current with the filtering and amplification circuit and, at each blade 53, 54, a zone of electrical contact 512 with the scalp.

At the contact with the scalp, the metal will be able to be treated (silver/silver chloride plating, for example).

In the example represented in FIGS. 5A, 5B, the blade at the zone of contact with the scalp is slightly concave, which makes it possible to more naturally fit the form of the skull.

As illustrated in FIGS. 5A, 5B, the blades can have one or two points (541, 542 in FIG. 5B), one on each side of the sensor to keep the symmetry and allow the sensor to pivot relative to the support. The point on the bottom side of the sensor also serves to facilitate the penetration of the sensor into the hair to reach the scalp. The points are not necessarily conductive.

As illustrated in FIGS. 5A, 5B, the blades can be solid, which gives them a better rigidity.

Figure 5C:
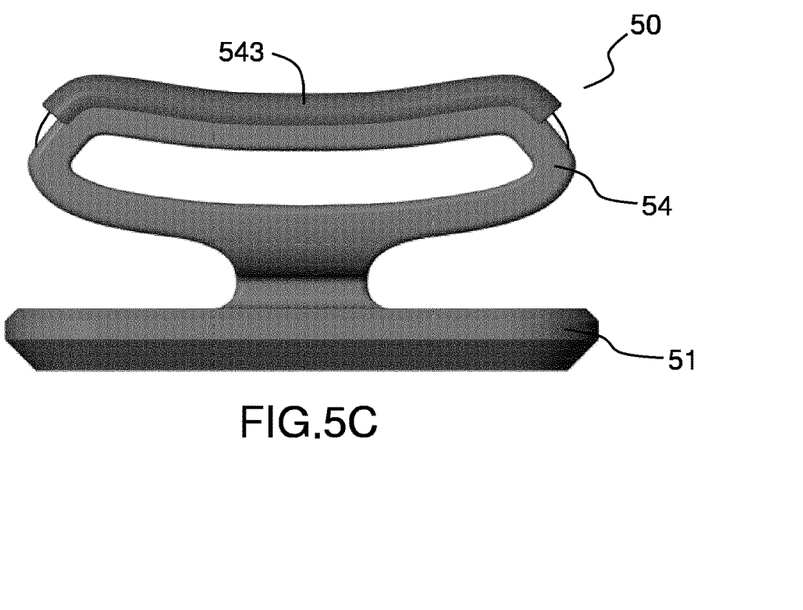

FIG. 5C represents another exemplary embodiment of a sensor according to the present description. In this example, a conductive polymer, for example of PEDOT:PSS type, forms a flexible layer 543 which can be flattened on the scalp when a pressure is exerted and thus increase the contact surface area. The pressure is then better distributed on the skull, which makes the device more comfortable. Also, the contact surface area is greater, and the electrical resistance at the interface between the skull and the sensor is lower, which results in a better passage of the EEG signals in the sensor. Furthermore, the flexible polymer absorbs the micro-movements of the device relative to the scalp of the user and improves the stability of the electrical properties at the interface, which makes it possible to reduce the artefacts, that is to say the variations in the measurements, that are independent of the cerebral activity. Finally, these polymers have the advantage of being biocompatible.

Obviously, other forms and/or coatings are possible to form a sensor according to the present description. For example, the metal part of the sensor could be dispensed with by using a conductive material other than metal for the structure of the sensor (such as a conductive polymer).

Figure 6:
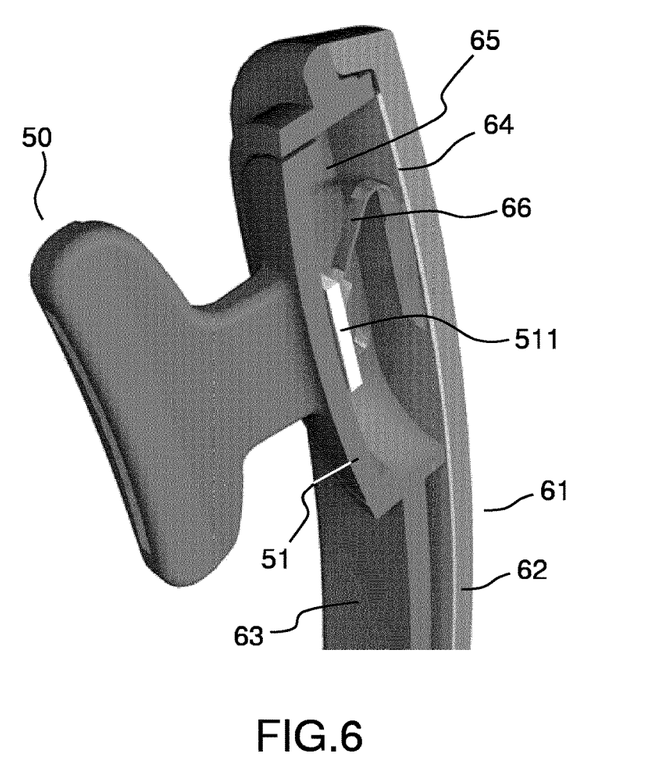
FIG. 6, an embodiment of a sensor movably mounted on the flexible support.

FIG. 6 illustrates an example of a sensor 50 as described in FIGS. 5A, 5B mounted in a flexible support 61. As illustrated in FIG. 6, the base 51 of the sensor can be mounted removably in a recess 65 of the support formed between two plates 62, 63 of the support. The sensor 50 is movably mounted relative to the flexible support 61 to allow the device to be adapted to different skull forms. A metal blade 66 with spring effect ensures the electrical contact between the conductive zone 511 of the base and the filtering and amplification circuit situated on a flexible printed circuit 64 internal to the flexible support. The blade 66 ensures, by virtue of a contact point with the base of the sensor, a translational mobility on the vertical axis (at right angles to the support), and rotational mobility about the 2 horizontal axes. These mobilities are constrained by the forms of the sensor and of its support.

Although described through a certain number of detailed exemplary embodiments, the portable devices for acquiring electroencephalographic signals according to the present description comprise different variants, modifications and refinements which will be evident to a person skilled in the art, given that these different variants, modifications and refinements form part of the scope of the subject matter of the present description, as defined by the following claims.

The invention claimed is:

1. A portable device for acquisition of electroencephalographic (EEG) signals emitted by a user, the device comprising:
    a flexible support intended to fit a localized region of a skull of the user;
    a set of sensors for detecting electrical signals generated by neuronal activity of the user, arranged on the support so as to form contacts with a scalp of the user when the device is worn by the user, each sensor comprising a plurality of conductive blades arranged parallel to one another, each conductive blade being concave at a zone of contact with the scalp, the conductive blades including at least one point configured to make initial contact with the scalp when the portable device is positioned on the skull, the at least one point being non-conductive;
    for each sensor, an electronic circuit for filtering and amplifying the electrical signals detected by the sensor, the electronic circuit being incorporated in the flexible support and forming with the sensor an active electrode; and
    a housing comprising an electronic system for processing the signals from each electronic circuit, the housing being linked mechanically to the flexible support to form, with the support, a means of attachment to a garment or accessory intended to be worn by the user.

2. The portable device as claimed in claim 1, wherein the flexible support is openwork and comprises a plurality of branches on which at least some of said sensors are arranged.

3. The portable device as claimed in claim 2, wherein the flexible support comprises a central part, the branches being linked to said central part by means of flexible lateral branches.

4. The portable device as claimed in claim 1, wherein the flexible support and the housing are linked mechanically by a flexible attachment point, making it possible to form a clip-form attachment means.

5. The portable device as claimed in claim 1, wherein each sensor is movably mounted on said flexible support.

6. The portable device as claimed in claim 1, wherein each sensor comprises a base intended to be arranged in a recess of said flexible support, in electrical contact with said electronic circuit.

7. The portable device as claimed in claim 6, wherein said electrical contact is ensured by a spring finger, forming a contact point with said base.

8. The portable device as claimed in claim 1, wherein the conductive blades comprise a conductive polymer coating forming a conductive layer intended to enter into contact with the scalp of the user.

9. A connected garment for acquiring electroencephalographic (EEG) signals comprising a portable device as claimed in claim 1.

10. A method for acquiring electroencephalographic (EEG) signals emitted by a user by means of a portable device as claimed in claim 1, comprising:
    measuring of electrical signals generated by the neuronal activity of the user by means of said sensors in contact with the scalp of the user; and
    processing of the electrical signals from said electronic circuits by means of the electronic system arranged in said housing.

* * * * *